United States Patent
Barnes et al.

(10) Patent No.: US 9,849,043 B2
(45) Date of Patent: Dec. 26, 2017

(54) ABSORBENT ARTICLE HAVING A PROTECTED FASTENING SYSTEM

(71) Applicant: Kimberly-Clark Worldwide, Inc., Neenah, WI (US)

(72) Inventors: Nickolas Paul Barnes, Neenah, WI (US); Patrick Robert Lord, Neenah, WI (US); Bonnie Lynn VandenPlas, North Ogden, UT (US); Himanshi Arunkumar Patel, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 43 days.

(21) Appl. No.: 15/102,620

(22) PCT Filed: Oct. 14, 2015

(86) PCT No.: PCT/US2015/055539
§ 371 (c)(1),
(2) Date: Jun. 8, 2016

(87) PCT Pub. No.: WO2016/069269
PCT Pub. Date: May 6, 2016

(65) Prior Publication Data
US 2017/0027775 A1   Feb. 2, 2017

Related U.S. Application Data

(60) Provisional application No. 62/073,529, filed on Oct. 31, 2014.

(51) Int. Cl.
*A61F 13/56* (2006.01)
*A61F 13/62* (2006.01)

(52) U.S. Cl.
CPC ........ *A61F 13/622* (2013.01); *A61F 13/5633* (2013.01); *A61F 13/5644* (2013.01)

(58) Field of Classification Search
CPC .............. A61F 13/5633; A61F 13/5644; A61F 13/581; A61F 13/62; A61F 13/622;
(Continued)

(56) References Cited

U.S. PATENT DOCUMENTS 3,848,594 A   11/1974 Buell
4,010,754 A   3/1977 Pieniak
(Continued)

FOREIGN PATENT DOCUMENTS

EP   0217032 A2   4/1987
EP   0233704 B1   7/1992
(Continued)

*Primary Examiner* — Lynne Anderson
(74) *Attorney, Agent, or Firm* — Kimberly-Clark Worldwide, Inc.

(57) ABSTRACT

An absorbent article includes an absorbent assembly including longitudinally opposite ends, transversely opposite sides, a front waist region, a back waist region. The absorbent article also includes a pair of ears extending transversely outward from the opposite sides of the absorbent assembly in the back waist region, each of the ears comprising a loop fastening component. The absorbent article also includes a nonwoven shield coupled to the garment-facing surface of the outer cover and a hook material patch, wherein the hook material patch is disposed between the outer cover and the shield such that at least a portion of the plurality of hooks is accessible through an aperture, and such that at least a portion of the base layer edges is covered by the shield.

17 Claims, 7 Drawing Sheets

(58) Field of Classification Search
CPC .......... A61F 13/625; A61F 13/627; A61F 2013/5666; A61F 2013/5677
See application file for complete search history.

(56) References Cited

U.S. PATENT DOCUMENTS

| | | |
|---|---|---|
| 4,041,203 A | 8/1977 | Brock et al. |
| 4,050,462 A | 9/1977 | Woon et al. |
| 4,253,461 A | 3/1981 | Strickland et al. |
| 4,374,888 A | 2/1983 | Bornslaeger |
| 4,402,690 A | 9/1983 | Redfern |
| 4,500,316 A | 2/1985 | Damico |
| 4,581,772 A | 4/1986 | Smith |
| 4,585,448 A | 4/1986 | Enloe |
| 4,662,875 A | 5/1987 | Hirotsu et al. |
| 4,663,220 A | 5/1987 | Wisneski et al. |
| 4,699,622 A | 10/1987 | Toussant et al. |
| 4,701,179 A | 10/1987 | Kellenberger et al. |
| 4,753,650 A | 6/1988 | Williams |
| 4,766,029 A | 8/1988 | Brock et al. |
| 4,770,656 A | 9/1988 | Proxmire et al. |
| 4,773,906 A | 9/1988 | Krushel |
| 4,801,298 A | 1/1989 | Sorenson et al. |
| 4,846,815 A | 7/1989 | Scripps |
| 4,850,988 A | 7/1989 | Aledo et al. |
| 4,850,992 A | 7/1989 | Amaral et al. |
| 4,869,724 A | 9/1989 | Scripps |
| 4,894,060 A | 1/1990 | Nestegard |
| 4,923,456 A | 5/1990 | Proxmire |
| 4,936,840 A | 6/1990 | Proxmire |
| 4,938,753 A | 7/1990 | Van Gompel et al. |
| 4,940,464 A | 7/1990 | Van Gompel et al. |
| 4,946,527 A | 8/1990 | Battrell |
| 4,988,346 A | 1/1991 | Pfefferkorn |
| 5,019,072 A | 5/1991 | Polski |
| 5,019,073 A | 5/1991 | Roessler et al. |
| 5,046,272 A | 9/1991 | Vogt et al. |
| 5,069,678 A | 12/1991 | Yamamoto et al. |
| 5,104,116 A | 4/1992 | Pohjola |
| 5,108,384 A | 4/1992 | Goulait |
| 5,151,092 A | 9/1992 | Buell et al. |
| 5,169,706 A | 12/1992 | Collier, IV et al. |
| 5,176,670 A | 1/1993 | Roessler et al. |
| 5,176,671 A | 1/1993 | Roessler et al. |
| 5,213,881 A | 5/1993 | Timmons et al. |
| 5,224,405 A | 7/1993 | Pohjola |
| 5,226,992 A | 7/1993 | Morman |
| 5,231,738 A | 8/1993 | Higashinaka |
| 5,242,436 A | 9/1993 | Weil et al. |
| 5,260,015 A | 11/1993 | Kennedy et al. |
| 5,279,604 A | 1/1994 | Robertson et al. |
| 5,325,569 A | 7/1994 | Goulait et al. |
| 5,358,500 A | 10/1994 | Lavon et al. |
| 5,368,585 A | 11/1994 | Dokken |
| 5,370,634 A | 12/1994 | Ando et al. |
| 5,383,871 A | 1/1995 | Carlin et al. |
| 5,392,498 A | 2/1995 | Goulait et al. |
| 5,399,219 A | 3/1995 | Roessler et al. |
| 5,403,302 A | 4/1995 | Roessler et al. |
| 5,409,476 A | 4/1995 | Coates |
| 5,423,789 A | 6/1995 | Kuen |
| 5,464,688 A | 11/1995 | Timmons et al. |
| 5,518,795 A | 5/1996 | Kennedy et al. |
| 5,531,732 A | 7/1996 | Wood |
| 5,554,143 A | 9/1996 | Roe et al. |
| 5,593,401 A | 1/1997 | Sosalla et al. |
| 5,599,338 A | 2/1997 | Enloe |
| 5,603,794 A | 2/1997 | Thomas |
| 5,605,735 A | 2/1997 | Zehner et al. |
| 5,611,789 A | 3/1997 | Seth |
| 5,624,428 A | 4/1997 | Sauer |
| 5,624,429 A | 4/1997 | Long et al. |
| 5,643,651 A | 7/1997 | Murasaki |
| H1674 H | 8/1997 | Ames et al. |
| 5,669,120 A | 9/1997 | Wessels et al. |
| 5,674,215 A | 10/1997 | Roennberg |
| 5,685,873 A | 11/1997 | Bruemmer |
| 5,695,488 A | 12/1997 | Sosalla |
| 5,744,080 A | 4/1998 | Kennedy et al. |
| 5,759,317 A | 6/1998 | Justmann |
| 5,766,389 A | 6/1998 | Brandon et al. |
| 5,766,723 A | 6/1998 | Oborny et al. |
| 5,772,649 A | 6/1998 | Siudzinski |
| 5,782,819 A | 7/1998 | Tanzer et al. |
| 5,797,896 A | 8/1998 | Schmitz |
| 5,830,206 A | 11/1998 | Larsson |
| 5,846,262 A | 12/1998 | Sayama et al. |
| 5,851,467 A | 12/1998 | Murasaki |
| 5,858,515 A | 1/1999 | Stokes et al. |
| 5,984,911 A | 11/1999 | Siebers et al. |
| 5,997,522 A | 12/1999 | Provost et al. |
| 6,030,373 A | 2/2000 | Vangompel et al. |
| 6,045,543 A | 4/2000 | Pozniak et al. |
| 6,056,732 A | 5/2000 | Fujioka et al. |
| 6,063,066 A | 5/2000 | Inoue et al. |
| 6,099,516 A | 8/2000 | Pozniak et al. |
| 6,102,901 A | 8/2000 | Lord et al. |
| 6,142,983 A | 11/2000 | Suprise et al. |
| 6,142,986 A | 11/2000 | Lord et al. |
| 6,174,303 B1 | 1/2001 | Suprise et al. |
| 6,174,476 B1 | 1/2001 | Kennedy et al. |
| 6,206,679 B1 | 3/2001 | Provost et al. |
| 6,248,419 B1 | 6/2001 | Kennedy et al. |
| 6,264,644 B1 | 7/2001 | Igaue et al. |
| 6,287,287 B1 | 9/2001 | Elsberg |
| 6,302,871 B1 | 10/2001 | Nakao et al. |
| 6,322,552 B1 | 11/2001 | Blenke et al. |
| 6,371,949 B1 | 4/2002 | Soga et al. |
| 6,371,951 B1 | 4/2002 | Koczab et al. |
| 6,387,085 B1 | 5/2002 | Van Gompel et al. |
| 6,402,731 B1 | 6/2002 | Suprise et al. |
| 6,406,466 B1 | 6/2002 | Pozniak et al. |
| 6,454,752 B1 | 9/2002 | Huang et al. |
| 6,491,675 B1 | 12/2002 | Shimada et al. |
| 6,508,797 B1 | 1/2003 | Pozniak et al. |
| 6,524,293 B1 | 2/2003 | Elsberg et al. |
| 6,524,294 B1 | 2/2003 | Hilston et al. |
| 6,544,242 B1 | 4/2003 | Kido et al. |
| 6,551,294 B1 | 4/2003 | Elsberg et al. |
| 6,554,816 B1 | 4/2003 | Olson |
| 6,572,601 B2 | 6/2003 | Suprise et al. |
| 6,575,951 B1 * | 6/2003 | Ono .......... A61F 13/505 604/385.14 |
| 6,595,977 B1 | 7/2003 | Luizzi, Jr. et al. |
| 6,613,032 B2 | 9/2003 | Ronnberg et al. |
| 6,648,866 B2 | 11/2003 | Magee et al. |
| 6,682,512 B2 | 1/2004 | Uitenbroek et al. |
| 6,730,069 B2 | 5/2004 | Tanzer et al. |
| 6,733,483 B2 | 5/2004 | Raufman et al. |
| 6,736,804 B1 | 5/2004 | Robertson et al. |
| 6,737,147 B2 | 5/2004 | Kennedy et al. |
| 6,849,067 B2 | 2/2005 | Fletcher et al. |
| 6,890,630 B2 | 5/2005 | Franklin et al. |
| 6,893,426 B1 | 5/2005 | Popp et al. |
| 6,916,750 B2 | 7/2005 | Thomas et al. |
| 6,932,802 B2 | 8/2005 | Luizzi, Jr. et al. |
| 6,945,968 B2 | 9/2005 | Svensson et al. |
| 6,972,012 B1 | 12/2005 | Pozniak et al. |
| 6,976,978 B2 | 12/2005 | Ruman et al. |
| 6,994,697 B2 | 2/2006 | Shimada et al. |
| 6,994,698 B2 | 2/2006 | Leak et al. |
| 7,014,906 B2 | 3/2006 | Tuman et al. |
| 7,018,368 B2 | 3/2006 | Van Gompel et al. |
| 7,032,278 B2 | 4/2006 | Kurtz, Jr. |
| 7,122,024 B2 | 10/2006 | Nakajima et al. |
| 7,150,730 B2 | 12/2006 | Hasler et al. |
| 7,150,732 B2 | 12/2006 | Yoshida et al. |
| 7,150,733 B2 | 12/2006 | Yamakawa et al. |
| 7,156,833 B2 | 1/2007 | Couture-Dorschner et al. |
| 7,162,780 B2 | 1/2007 | Martin et al. |
| 7,175,584 B2 | 2/2007 | Maxton et al. |
| 7,189,220 B2 | 3/2007 | Miyoshi et al. |
| 7,198,621 B2 | 4/2007 | Moser et al. |
| 7,201,744 B2 | 4/2007 | Van Gompel et al. |

(56) References Cited

U.S. PATENT DOCUMENTS

| | | |
|---|---|---|
| 7,207,979 B2 | 4/2007 | Price et al. |
| 7,211,072 B2 | 5/2007 | Nawata et al. |
| 7,244,382 B2 | 7/2007 | Tachauer et al. |
| 7,252,658 B2 | 8/2007 | Sayama |
| 7,275,290 B2 | 10/2007 | Clarner et al. |
| 7,344,525 B2 | 3/2008 | Linker, III et al. |
| 7,384,415 B2 | 6/2008 | Kline et al. |
| 7,422,783 B2 | 9/2008 | Tremblay et al. |
| 7,449,017 B2 | 11/2008 | Yoshida |
| 7,451,532 B2 | 11/2008 | Provost et al. |
| 7,455,665 B2 | 11/2008 | Wendelstorf et al. |
| 7,473,818 B2 | 1/2009 | Datta et al. |
| 7,534,481 B2 | 5/2009 | Seth et al. |
| 7,568,264 B2 | 8/2009 | Miyamoto et al. |
| 7,569,042 B2 | 8/2009 | Van Gompel et al. |
| 7,662,137 B2 | 2/2010 | Sayama et al. |
| 7,736,351 B2 | 6/2010 | Nigam et al. |
| 7,811,273 B2 | 10/2010 | Kline et al. |
| 7,828,784 B2 | 11/2010 | Popp et al. |
| 7,855,314 B2 | 12/2010 | Hanao et al. |
| 8,118,801 B2 | 2/2012 | Macura et al. |
| 8,211,077 B2 | 7/2012 | Sugiyama et al. |
| 8,353,891 B2 | 1/2013 | Hornung et al. |
| 8,395,017 B2 | 3/2013 | Nakahata et al. |
| 8,496,640 B2 | 7/2013 | Molander |
| 8,636,710 B2 | 1/2014 | Ellingson et al. |
| 9,301,887 B2 * | 4/2016 | Coates ............... A61F 13/505 |
| 9,597,237 B2 * | 3/2017 | Enz .................. A61F 13/5644 |
| 2002/0016581 A1 | 2/2002 | Kline et al. |
| 2002/0029441 A1 | 3/2002 | Shepard et al. |
| 2002/0032427 A1 | 3/2002 | Schmitz et al. |
| 2002/0095130 A1 | 7/2002 | Seitter et al. |
| 2002/0095132 A1 | 7/2002 | Ashton et al. |
| 2002/0107498 A1 | 8/2002 | Kling et al. |
| 2002/0123734 A1 | 9/2002 | Carlbark et al. |
| 2002/0138064 A1 | 9/2002 | Datta et al. |
| 2002/0165518 A1 | 11/2002 | Datta et al. |
| 2002/0169431 A1 | 11/2002 | Kline et al. |
| 2002/0173768 A1 | 11/2002 | Elsberg et al. |
| 2002/0174934 A1 | 11/2002 | Johnson et al. |
| 2003/0044578 A1 | 3/2003 | Nissing |
| 2003/0153891 A1 | 8/2003 | Molee |
| 2003/0233080 A1 | 12/2003 | Backman et al. |
| 2004/0016499 A1 | 1/2004 | Miyamoto et al. |
| 2004/0122400 A1 | 6/2004 | Hancock-Cooke et al. |
| 2004/0122413 A1 | 6/2004 | Roessler et al. |
| 2004/0129592 A1 | 7/2004 | Otsubo |
| 2004/0158224 A1 | 8/2004 | Kline et al. |
| 2004/0187275 A1 | 9/2004 | Kennedy et al. |
| 2004/0243091 A1 | 12/2004 | Mitsui et al. |
| 2004/0261233 A1 | 12/2004 | Kingsford et al. |
| 2005/0015069 A1 | 1/2005 | Hamilton et al. |
| 2005/0027271 A1 | 2/2005 | Popp et al. |
| 2005/0043700 A1 | 2/2005 | Otsubo et al. |
| 2005/0090793 A1 | 4/2005 | Winqvist |
| 2005/0143710 A1 | 6/2005 | Van Gompel et al. |
| 2005/0148976 A1 | 7/2005 | Van Gompel et al. |
| 2005/0148977 A1 | 7/2005 | Van Gompel et al. |
| 2005/0148982 A1 | 7/2005 | Van Gompel et al. |
| 2005/0148985 A1 | 7/2005 | Bronk et al. |
| 2005/0148986 A1 | 7/2005 | Collins et al. |
| 2005/0217791 A1 | 10/2005 | Costello et al. |
| 2005/0222550 A1 | 10/2005 | Mitsui et al. |
| 2005/0222551 A1 | 10/2005 | Otsubo |
| 2006/0004337 A1 | 1/2006 | Datta |
| 2006/0025737 A1 | 2/2006 | Song et al. |
| 2006/0069376 A1 | 3/2006 | Miller et al. |
| 2006/0069378 A1 | 3/2006 | Winkel et al. |
| 2006/0241561 A1 | 10/2006 | De Angelis |
| 2006/0247594 A1 | 11/2006 | Nickel et al. |
| 2006/0247597 A1 | 11/2006 | Hogan et al. |
| 2006/0264861 A1 | 11/2006 | Lavon et al. |
| 2006/0266465 A1 | 11/2006 | Meyer |
| 2006/0293639 A1 | 12/2006 | Van Gompel et al. |
| 2007/0032773 A1 | 2/2007 | Magee et al. |
| 2007/0083177 A1 | 4/2007 | Takino et al. |
| 2007/0093769 A1 | 4/2007 | Kline et al. |
| 2007/0112321 A1 | 5/2007 | Goates et al. |
| 2007/0157441 A1 | 7/2007 | Kline et al. |
| 2007/0250026 A1 | 10/2007 | Venturino et al. |
| 2008/0058753 A1 | 3/2008 | Dalal |
| 2008/0077101 A1 | 3/2008 | Waksmundzki et al. |
| 2008/0086104 A1 | 4/2008 | Karlsson |
| 2008/0091163 A1 | 4/2008 | Fujioka |
| 2008/0097363 A1 | 4/2008 | Fernfors et al. |
| 2008/0114323 A1 | 5/2008 | Kline et al. |
| 2008/0132863 A1 | 6/2008 | Waksmundzki et al. |
| 2008/0154227 A1 | 6/2008 | Andersson et al. |
| 2008/0172840 A1 | 7/2008 | Kacker et al. |
| 2008/0312624 A1 | 12/2008 | Hundorf et al. |
| 2009/0076783 A1 | 3/2009 | Babusik et al. |
| 2009/0198207 A1 | 8/2009 | Torigoshi et al. |
| 2009/0299317 A1 | 12/2009 | Flannery |
| 2009/0299318 A1 | 12/2009 | Faulks et al. |
| 2009/0299322 A1 | 12/2009 | Faulks et al. |
| 2009/0299323 A1 | 12/2009 | Schlinz et al. |
| 2010/0179503 A1 | 7/2010 | Roe et al. |
| 2010/0234822 A1 | 9/2010 | Baeck |
| 2010/0241096 A1 | 9/2010 | Lavon et al. |
| 2011/0100526 A1 | 5/2011 | Umebayashi |
| 2011/0168318 A1 | 7/2011 | Nilsson et al. |
| 2012/0157958 A1 | 6/2012 | Tenorio et al. |
| 2012/0245548 A1 | 9/2012 | Matsushima et al. |
| 2013/0067701 A1 | 3/2013 | Grady et al. |
| 2013/0211361 A1 | 8/2013 | Anderson et al. |
| 2013/0310794 A1 | 11/2013 | Faulks et al. |
| 2014/0046284 A1 | 2/2014 | Dougherty, Jr. et al. |
| 2014/0046287 A1 | 2/2014 | Martin et al. |
| 2014/0350507 A1 | 11/2014 | Pariseau et al. |
| 2015/0025491 A1 | 1/2015 | Sakaguchi et al. |
| 2015/0032075 A1 | 1/2015 | Popp et al. |
| 2015/0126947 A1 | 5/2015 | Stabelfeldt et al. |
| 2015/0126950 A1 | 5/2015 | Hancock-Cooke et al. |

FOREIGN PATENT DOCUMENTS

| | | |
|---|---|---|
| EP | 0476992 B1 | 7/1995 |
| EP | 1600132 A1 | 11/2005 |
| EP | 1299063 B1 | 3/2006 |
| EP | 1688117 A1 | 8/2006 |
| EP | 2335504 B1 | 4/2013 |
| GB | 2033210 A | 5/1980 |
| GB | 2 127 674 A | 4/1984 |
| JP | 01-062303 U1 | 4/1989 |
| JP | 01-092403 A | 4/1989 |
| JP | 02-088626 U1 | 7/1990 |
| JP | 07-227403 A | 8/1995 |
| JP | 08-005691 Y2 | 2/1996 |
| JP | 08-252281 A | 10/1996 |
| JP | 2003-079666 A | 3/2003 |
| JP | 2005-040231 A | 2/2005 |
| JP | 2006-280664 A | 10/2006 |
| JP | 2007-209457 A | 8/2007 |
| JP | 2008-079867 A | 4/2008 |
| WO | WO 1993/025171 A1 | 12/1993 |
| WO | WO 1997/046197 A1 | 12/1997 |
| WO | WO 1998/035642 A1 | 8/1998 |
| WO | WO 2000/027328 A1 | 5/2000 |
| WO | WO 2000/035397 A1 | 6/2000 |
| WO | WO 2001/088245 A2 | 11/2001 |
| WO | WO 2005/110314 A1 | 11/2005 |
| WO | WO 2013/097878 A1 | 7/2013 |
| WO | WO 2013/115347 A1 | 8/2013 |

* cited by examiner

ABSORBENT ARTICLE HAVING A PROTECTED FASTENING SYSTEM

The present application claims priority to U.S. Provisional Application No. 62/073,529, filed Oct. 31, 2014, the contents of which are hereby incorporated by reference in a manner consistent with the present application.

BACKGROUND

The present disclosure relates generally to absorbent articles intended for personal wear, and more particularly to disposable absorbent articles having a fastening system for selectively fastening and refastening the article about the wearer.

Many absorbent articles intended for personal wear, such as diapers, training pants, feminine hygiene products, adult incontinence products, bandages, medical garments and the like are designed to be sufficiently absorbent to absorb moisture from liquid body exudates including urine, menses, blood, etc., away from the wearer to reduce skin irritation caused by prolonged wetness exposure. Diapers, as an example, are typically placed and secured on a wearer using a set of primary fastening tabs, such as adhesive tabs or mechanical (e.g., hook or loop) fastening system tabs, and left in place to absorb insults as well as to contain fecal waste.

For articles where the attachment is refastenable, such as diapers and some training pants, pop-opens (separation of the fasteners) can sometimes occur as a result of stresses placed on the attachment by movement of the wearer. For example, and particularly for absorbent articles employing only one fastening system, as an infant or other wearer of the absorbent article moves about (e.g., crawls, walks, runs, bends, etc.) the shear stress placed on the fastening system due to the infant's movement can cause fastening tabs or the like to loosen or even come unfastened completely, resulting in an absorbent article that tends to leak, sag, or fall off of a wearer.

Secondary fasteners can be used to alleviate these issues, but secondary fasteners have a higher risk of red marking on the baby's skin compared to the primary fastener. Fastening features can be arranged to limit red marking, but these compromises do not maintain the fit on the baby was well as they could. Even in these compromises, there remains a risk that both hook fasteners can cause red marking on baby's skin.

There is a need, therefore, for an improved fastening system provided on an absorbent article that provides for increased protection against leakage and secure attachment of the absorbent article without the associated discomfort drawbacks discussed above.

SUMMARY

The present disclosure describes an absorbent article including an absorbent assembly including longitudinally opposite ends, transversely opposite sides, a front waist region, a back waist region, and a crotch region extending longitudinally between and interconnecting the front and back waist regions, a liquid permeable bodyside liner for facing a wearer, an outer cover with a garment-facing surface facing away from the wearer, an absorbent body disposed between the bodyside liner and outer cover, at least one of the bodyside liner and outer cover defining the longitudinally opposite ends and transversely opposite sides of the absorbent assembly, the absorbent body having a pair of longitudinally extending sides and a pair of transversely extending ends, each of the longitudinally extending sides of the absorbent body being spaced inward from a respective one of the transversely opposite sides of the absorbent assembly. The absorbent article also includes a pair of ears extending transversely outward from the opposite sides of the absorbent assembly in the back waist region, each of the ears comprising a loop fastening component, and a pair of spaced-apart hook fastening components disposed on the outer cover in the front waist region of the absorbent assembly, each of the hook fastening components being selectively engageable with a respective one of the loop fastening components in a wear configuration of the article. The absorbent article also includes a nonwoven shield coupled to the garment-facing surface of the outer cover, wherein the shield has an aperture therethrough, wherein each hook fastening component includes a hook material patch including a base layer having a hook surface, a non-hook surface opposite the hook surface, and base layer edges therebetween, and a plurality of hooks affixed to the hook surface, wherein the hook material patch is disposed between the outer cover and the shield such that at least a portion of the plurality of hooks is accessible through the aperture, and such that at least a portion of the base layer edges is covered by the shield.

The present disclosure also describes an absorbent article including an absorbent assembly including a front waist region, a back waist region, and a crotch region extending longitudinally between and interconnecting the front and back waist regions, a liquid permeable bodyside liner for facing a wearer, an outer cover with a garment-facing surface facing away from the wearer, and an absorbent body disposed between the bodyside liner and outer cover; and a pair of ears extending transversely outward from the opposite sides of the absorbent assembly in the back waist region, each of the ears comprising a loop fastening component. The absorbent article also includes a pair of spaced-apart hook fastening components disposed on the outer cover in the front waist region of the absorbent assembly, each of the hook fastening components being selectively engageable with a respective one of the loop fastening components in a wear configuration of the article; and a nonwoven shield coupled to the garment-facing surface of the outer cover, wherein the shield has an aperture therethrough. Each hook fastening component includes a hook material patch comprising a plurality of hooks and a hook material edge, wherein the hook material patch is disposed between the outer cover and the shield such that at least a portion of the plurality of hooks is accessible through the aperture, and such that a portion of the shield adjacent the aperture covers the hook material edge.

The present disclosure also describes an absorbent article including an absorbent assembly including a front waist region, a back waist region, and a crotch region extending longitudinally between and interconnecting the front and back waist regions, a liquid permeable bodyside liner for facing a wearer, an outer cover with a garment-facing surface facing away from the wearer, and an absorbent body disposed between the bodyside liner and outer cover; and a pair of ears extending transversely outward from the opposite sides of the absorbent assembly in the back waist region, each of the ears comprising a loop fastening component. The absorbent article also includes a pair of spaced-apart hook fastening components disposed on the outer cover in the front waist region of the absorbent assembly, each of the hook fastening components being selectively engageable with a respective one of the loop fastening components in a wear configuration of the article; and a nonwoven shield coupled to the garment-facing surface of the outer cover, wherein the shield has two curvilinear apertures therethrough. Each hook fastening component includes a hook material patch including a base layer having a hook surface, a non-hook surface opposite the hook surface, and base layer edges therebetween, and a plurality of hooks affixed to the hook surface, wherein the hook material patch is disposed between the outer cover and the shield such that at least a portion of the plurality of hooks is accessible through an aperture, and such that at least a portion of the base layer edges is covered by the shield.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
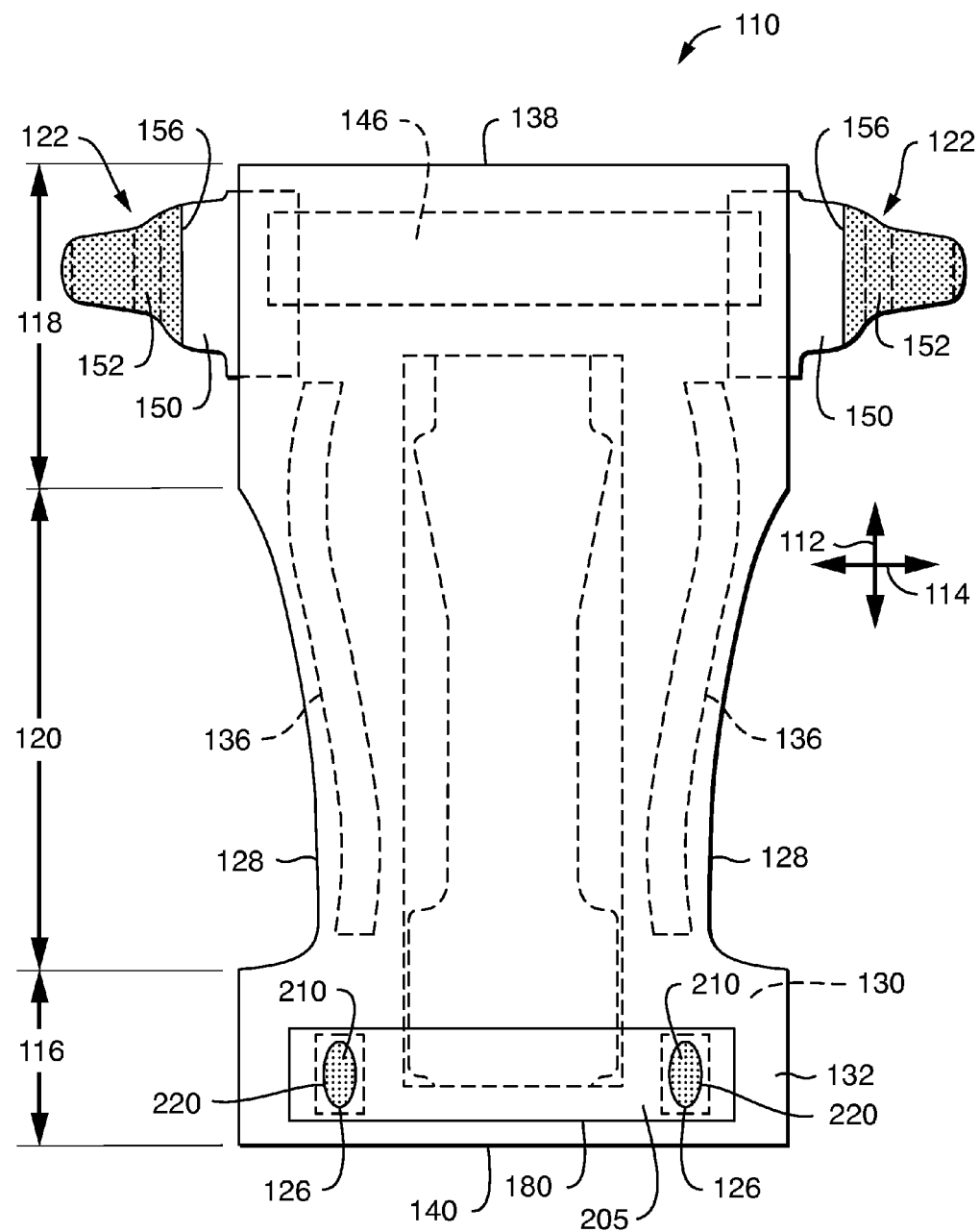
FIG. 1 is a top plan view of a diaper according to one aspect of the present disclosure in an unfolded and laid flat condition to show an outer surface of the diaper that faces away from the wearer when the diaper is worn.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

According to some aspects of the disclosure, an absorbent article is provided that overcomes at least some of the deficiencies of the conventional diapers described above. More particularly, according to some aspects of the disclosure, the absorbent article includes a secondary fastening system in order to securely attach the absorbent article around the waist of a wearer, but that includes improved pliability over known fastening systems such that the absorbent article remains securely fastened even as the wearer crawls, walks, runs, bends, etc. The secondary fastening system can be constructed of suitable materials and disposed in a suitable position relative to other components of the absorbent article such that the absorbent article can be readily packaged or used without the drawbacks of the known diapers discussed above.

Hook material, particularly the edges of hook material, can cause irritation and redness if it comes into contact with a wearer's skin. There are two ways that the hook material edges can come in contact with the baby's skin. If the outer cover material near the wearer's hip folds under, then hook material edges and corners are exposed to the wearer's skin. Also, if the diaper is put on the wearer incorrectly where the hook fastener flips towards the skin side, then the hook will be fully or partially exposed to the wearer's skin.

Figure 2:
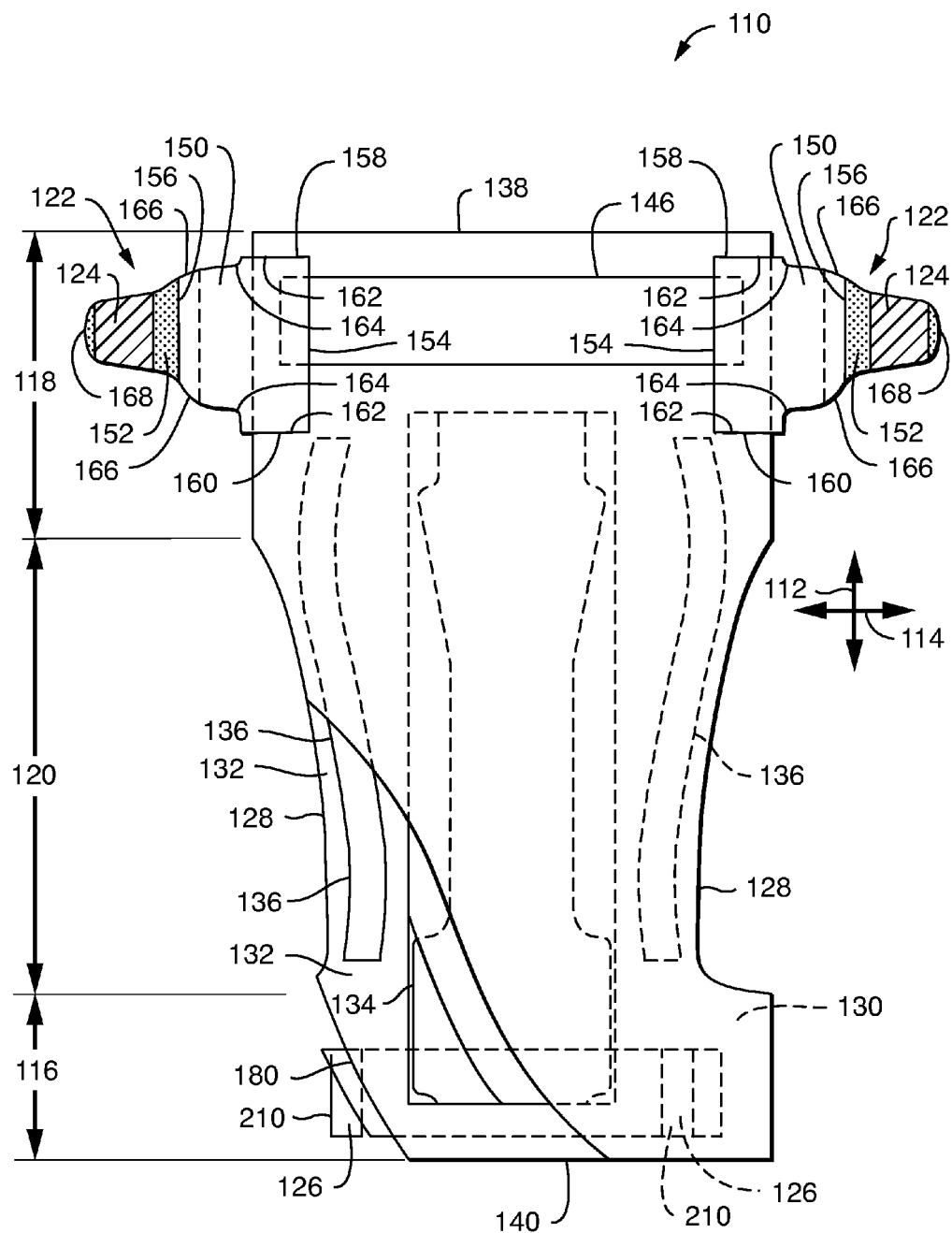
FIG. 2 is a bottom plan view of the diaper of FIG. 1 in an unfolded and laid flat condition to show an inner surface of the diaper that faces towards the wearer when the diaper is worn.

These features will become more apparent with reference to the accompanying drawings. FIGS. 1 and 2 illustrate one suitable aspect of a diaper (broadly, "an absorbent article"), indicated generally at 110, in an unfolded and laid flat condition to show an outer surface of the diaper that faces away from the wearer when the diaper is worn (FIG. 1) and an inner surface of the diaper that faces the wearer when the diaper is worn (FIG. 2). Portions of the diaper 110 illustrated in FIG. 2 are cut away to illustrate underlying structures. The diaper 110 has a longitudinal direction 112 and a lateral direction 114. While the present description will be made in the context of a diaper 110, it should be understood that the present disclosure is also applicable to other personal care absorbent articles, such as adult incontinence garments, children's training pants, swim pants, and the like.

In one suitable aspect, the diaper 110 is a disposable absorbent article. As used herein, the term "disposable absorbent article" refers to articles that absorb and contain body exudates and that are intended to be discarded after a limited period of use. The articles are not intended to be laundered or otherwise restored for reuse. The articles can be placed against or in proximity to the body of a wearer to absorb and contain various exudates discharged from the body. It is understood that in other suitable aspects, the diaper 110 can be reusable. That is, the diaper 110 can be intended for multiple uses without departing from some aspects of this disclosure.

In the longitudinal direction 112, the diaper 110 defines a front portion 116, a back portion 118, and a crotch portion 120 extending between and connecting the front portion and the back portion. The diaper 110 includes a bodyside liner 130, an outer cover 132, and an absorbent core 134 located between the bodyside liner 130 and the outer cover 132. The bodyside liner 130, outer cover 132 and absorbent core 134 collectively define an absorbent assembly. The absorbent assembly can be any suitable shape including, for example, generally I-shaped as illustrated in FIGS. 1 and 2. As used herein, reference to the front portion 116 refers to that part of the diaper 110 that is generally located on the front of a wearer when in use. Reference to the back portion 118 refers to the portion of the diaper 110 generally located at the back of the wearer when in use, and reference to the crotch portion 120 refers to that portion that is generally located between the legs of the wearer when in use.

In the illustrated aspect, the back portion 118 includes a straight back waist edge 138 and the front portion 116 includes a straight front waist edge 140. As used herein, "straight edge" refers to edges that are substantially free from curves, bends, angles, notches, or irregularities. It is understood, however, that the back waist 138 and the front waist 140 can be cut in any suitable shape as are known in the art (e.g., arcuate). As seen in FIGS. 1 and 2, the diaper 110 has opposite longitudinal side edges 128 that extend between the back waist edge 138 and the front waist edge 140. In the illustrated aspect, each of the side edges 128 includes an arcuate portion for defining a portion of a leg opening during wear of the diaper 110.

The bodyside liner 130 of the diaper 110, as illustrated in FIG. 2, defines a body facing surface that is intended to be worn adjacent and in directed contact with the body of the wearer.

The bodyside liner 130 is suitably compliant, soft feeling and nonirritating to the wearer's skin. The bodyside liner 130 is less hydrophilic than the absorbent core 134 and sufficiently porous to be liquid permeable. The bodyside liner 130 can be manufactured from a wide selection of suitable web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 130 is suitably adapted to isolate the wearer's skin from liquids and moisture held by the absorbent core 134.

The outer cover 132 of the diaper 110, which is illustrated in FIG. 1, defines a garment-facing surface that is intended to be worn adjacent the clothing of the wearer. In one suitable aspect, the outer cover 132 is a polyethylene film. In another suitable aspect, the outer cover 132 includes a woven or non-woven fibrous web layer that has been totally or partially constructed or treated to impart a desired level of liquid impermeability to selected regions of the outer cover 132 that are adjacent or proximate the absorbent core 134. For example, a cloth-like outer cover 132 can be composed of polypropylene spunbond fabric that is laminated and thermally bonded to a stretch-thinned polypropylene film. The outer cover 132 can include a micro-porous, "breathable" material that permits vapors to escape from diaper 110 while still preventing liquid exudates from passing through. For example, the outer cover 132 can be composed of a microporous polymer film or a nonwoven fabric that has been coated or otherwise treated to impart a desired level of liquid impermeability. The outer cover 132 can also be embossed or otherwise provided with a matte finish to exhibit a more aesthetically pleasing appearance.

The bodyside liner 130 and the outer cover 132 are generally joined in facing relationship with the absorbent core 134 located therebetween. The bodyside liner 130 and the outer cover 132 can be joined to each other around the outer periphery of the diaper 110 by any means known to those skilled in the art such as adhesive bonds, ultrasonic bonds, thermal bonds, and the like, and combinations thereof. As used herein, the term "join", and derivatives thereof, encompass configurations wherein an element is directly secured to the other element by affixing the element directly to the other element, and configurations wherein the element is indirectly secured to the other element by affixing the element to intermediate member(s) that in turn are affixed to the other element.

As mentioned above, the absorbent core 134 is positioned between the bodyside liner 130 and the outer cover 132. The absorbent core 134 is generally conformable and capable of absorbing and retaining liquid body exudates. The absorbent core 134 can include superabsorbent material, staple fibers, binder fibers, and the like, and combinations thereof as is known in the art. The absorbent core 134 can have any of a number of shapes and sizes. For example, the composite absorbent core 134 can be rectangular, I-shaped, or T-shaped. The size and absorbent capacity of the absorbent core 134 should be compatible with the size of the intended wearer and the fluid loading imparted by the intended use of the diaper.

In one suitable aspect, the diaper 110 can include a surge portion (not shown) disposed between the absorbent core 134 and the bodyside liner 130. The surge portion serves to quickly collect and temporarily hold liquids discharged by the wearer and then release the liquids to the absorbent core 134. Various woven and nonwoven materials can be used to construct the surge portion. For example, the surge portion can be a layer of a spunbonded or meltblown web of polyolefin fibers. The surge portion can also be a bonded carded web of natural and synthetic fibers. The surge portion can be a substantially hydrophobic material and, optionally, can be treated with a surfactant or otherwise to impart a desired level of wettability and hydrophilicity.

The diaper 110 includes a pair of elasticized, longitudinally-extending leg cuffs 136. The leg cuffs 136 are adapted to fit about the legs of a wearer in use and serve as a mechanical barrier to the lateral flow of body exudates. In one suitable aspect, the leg cuffs 136 can be formed by portions of the outer cover 132, and/or bodyside liner 130, which extend beyond the longitudinal sides of the absorbent core 134. In another suitable aspect, the leg cuffs 136 can be formed from separate materials (e.g., stands of leg elastics) joined to the outer cover 132 and/or the bodyside liner 130.

The diaper 110 can further include front waist elastic (not shown) and/or back waist elastic 146. In the illustrated aspect, for example, the diaper 110 has back waist elastic 146 but not front waist elastic. The back waist elastic 146 is arranged to draw and hold the diaper 110 against the wearer, particularly against the waist of the wearer, as will be more fully discussed.

Materials suitable for use in forming leg cuffs 136 and/or waist elastics 146 are known to those skilled in the art. Examples of such materials are strands or ribbons of a polymeric, elastomeric material that are adhered to the diaper 110 in a stretched position, or that are attached to the diaper while the diaper is pleated, such that elastic constrictive forces are imparted to the diaper. The leg cuffs 136 and/or waist elastics 146 can have any configuration that provides the desired performance. The leg cuffs 136 can be generally straight or optionally curved (as illustrated in FIGS. 1 and 2) to more closely fit the contours of the legs of the wearer. As used herein, "elastic," "elastomeric," and the like refer to the ability of a material or composite to be elongated by at least about 50 percent and upon relaxation to return to within at least 50 percent of its original length.

The leg cuffs 136 and/or waist elastics 146 can be attached to the diaper 110 in any way known to those skilled in the art. For example, the leg cuffs 136 and/or waist elastics 146 can be joined to the diaper 110 by ultrasonic bonding, thermal bonding, adhesive bonding, and the like, and combinations thereof.

The diaper 110 can also include a pair of containment flaps (not shown) that extend longitudinally along the diaper and are adapted to provide a barrier to the lateral flow of body exudates. The containment flaps can be connected to the bodyside liner 130 or other components as is well known in the art. Suitable configurations of the containment flaps are described, for example, in U.S. Pat. No. 5,599,338 issued Feb. 4, 1997, to K. Enloe, the entirety of which is incorporated herein by reference.

As seen in FIGS. 1 and 2, the back portion 118 of the diaper includes a pair of back ears, indicated generally at 122. In one suitable aspect, the back ears 122 can be formed from extensions of the bodyside liner 130, the outer cover 132, or combinations of both the bodyside liner and the outer cover 132. In another suitable aspect, and as illustrated in FIGS. 1 and 2, the back ears 122 can be formed as separate components and attached to the bodyside liner 130, the outer cover 132, or both the bodyside liner and the outer cover 132 as is known in the art. In the illustrated aspect, the back ears 122 are attached to the body-facing surface of the bodyside liner 130 such that the attached portion of the ears 122 are disposed between the wearer's body and bodyside liner when the diaper 110 is worn.

In one suitable aspect, each of the back ears 122 includes an elastomeric portion 150, a non-elastomeric portion 152, and a primary first fastening component 124 mounted to the non-elastomeric portion (FIG. 2). Each of the elastomeric portions 150 has a proximal edge 154, an opposed distal edge 156, an upper edge 158, and a lower edge 160. As seen in FIG. 2, the proximal edge 154 of each of the elastomeric portions 150 is spaced inward from the respective side edge 128 of the diaper 110 such that a portion of the elastomeric portion overlaps the bodyside liner 130. The part of each of the elastomeric portions 150 overlapping the bodyside liner 130 is bonded (e.g., adhesive bonding, thermal bonding, both thermal and adhesive bonding) to at least the bodyside liner 130. In another suitable aspect, the elastic component 150 can be eliminated and the entire back ear 122 can be constructed from the non-elastic component 152.

In the aspect illustrated in FIGS. 1 and 2, the proximal edge 154 and the distal edge 156 of each of the elastomeric portions 150 are generally parallel with respect to each other, and both are straight (i.e., linear). In one suitable aspect, the proximal edge 154 has a length from about 2 inches (5.1 centimeters) to about 7 inches (17.8 centimeters), preferably from about 3 inches (7.6 centimeters) to about 6 inches (15.2 centimeters), and more preferably from about 3.5 inches (8.9 centimeters) to about 5.5 inches (14.0 centimeters). The distal edge 156 has a length from about 0.25 inch (0.635 centimeter) to about 6 inches (15.24 centimeters), and preferably from about 1 inch (2.54 centimeters) to about 3 inches (7.6 centimeters). Further, the ratio of the length of the distal edge 156 to the proximal edge 154 is suitably from about 1:28 to about 3:4, and, and preferably from about 1:10 to about 2:3, and more preferably from about 1:4 to about 1:2.

Both the upper and lower edges 158, 160 have first segments 162 that are generally parallel to each other and generally perpendicular to the respective proximal edges 154. Each of the first segments 162 generally correspond to the part of each of the elastomeric portions 150 that overlap the bodyside liner 130. In the illustrated aspect, the first segments 162 of the upper edges 158 of the elastomeric portion 150 are spaced from the back waist edge 138. It is understood, however, that the first segments 162 can be aligned with the back waist edge 138 of the diaper 110.

Second segments 164 of each of the upper and lower edges 158, 160 are generally coaxial and extend towards each other generally perpendicular to the first segments 162. In the illustrated aspect, the second segment 164 of the lower edge 160 has a length greater than the length of the second segment of the upper edge 158. It is understood, however, that the second segments 164 of the upper and lower edges 158, 160 can have any suitable length.

Each of the illustrated elastomeric portions 150 includes an arcuate third segment 166 interconnecting the second segments 164 to the respective distal edge 156. In the illustrated aspect, the third segments 166 are generally mirror images of each other. It is understood, however, that the third segments 166 can have any suitable shape and that the third segments of the upper edges 158 can have a shape that is different that the shape of the third segments of the lower edges 160.

The elastomeric portions 150 of the back ears 122 can be formed from any type of elastomeric material capable of performing as described herein. In one suitable aspect, the elastomeric material will be stretchable in at least one direction (e.g., in the lateral direction 114 of the diaper 110 as viewed in FIGS. 1 and 2) and alternatively, the elastomeric material will be stretchable in two directions (e.g., in both the longitudinal direction 112 and the lateral direction of the diaper as viewed in FIGS. 1 and 2). Suitably when the elastomeric material is stretchable in a single direction, the stretch direction of the elastomeric material will be oriented so as to provide elastomeric forces that tend to pull the front and rear portions of the article towards one another such that the article is maintained about the waist of a wearer.

In one suitable aspect, the elastomeric material from which the elastomeric portions 150 of the back ears 122 are formed is capable of being elongated by at least about 50 percent, alternatively by at least about 100 percent, alternatively by at least about 130 percent. After elongation to 50 percent (if the elastomeric material is capable of being elongated to no more than 100 percent) or 100 percent (if the elastomeric material is capable of being elongated to more than 100 percent), the elastomeric material suitably recovers to at least about 50 percent of its original length, alternatively to at least about 80 percent of its original length. The elastomeric material can be an inherently elastomeric material, that is, one that is formed in an elastomeric state, or can be rendered elastomeric through processing subsequent formation. For example, the elastomeric material can be heat or pressure activated. The elastomeric portions 150 of the back ears 122 can be formed from a stretch-bonded-laminate (SBL) material, a neck-bonded-laminate (NBL) material, an elastomeric film, an elastomeric foam material, or the like.

Each of the non-elastomeric portions 152 of the back ears 122 is attached to a respective one of the elastomeric portions 150, and the primary first fastening components 124 (such as a hook material) are in turn disposed on the non-elastomeric portions. As illustrated in FIGS. 1 and 2, the non-elastomeric portions 152 of the back ears 122 extend in part transversely outward of the respective elastomeric portion 150 and the primary first fastening component 124 of each of the non-elastomeric portions are configured for engaging a loop component disposed in the front waist region 116 of the diaper 110 in the wear configuration, as will be discussed more fully.

As seen best in FIG. 2, each of the illustrated non-elastomeric portions 152 further include a grip region 168 transversely outward of the primary first fastening component 124 for use in manually gripping and manipulating the non-elastomeric portion and more broadly the respective back ear 122 relative to the diaper 110. The grip region 168 is non-attachable to the diaper 110. The term "non-attachable" as used in this instance means that the grip region 168 is not releasably or otherwise removably attachable to the diaper 110. In one aspect, the grip region 168 extends transversely outward from the respective primary first fastening component 124 a distance of at least about 1 mm, such as in the range of about 1 mm to about 10 mm to provide sufficient unattached material for readily gripping and pulling on the non-elastomeric portion 152.

Figure 3:
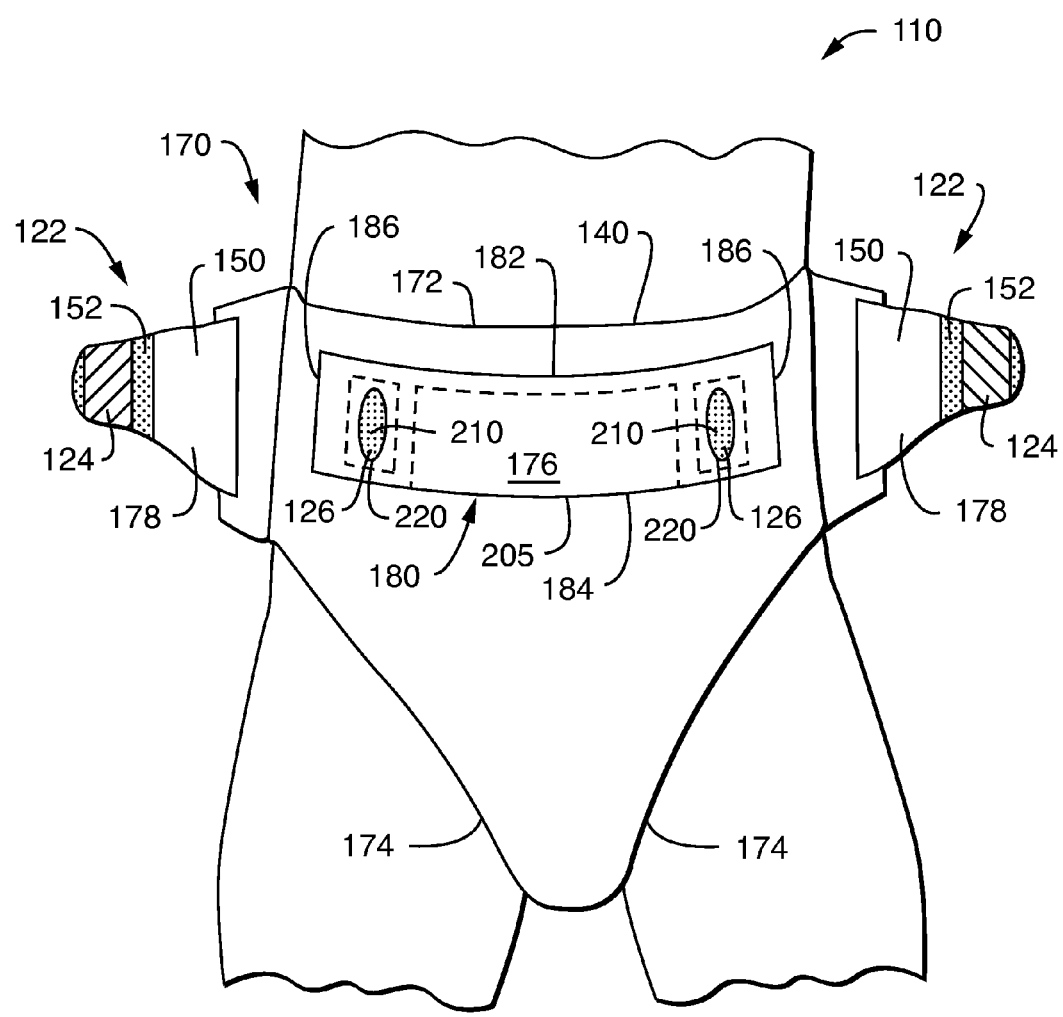
FIG. 3 is a front view of the diaper of FIG. 1 in a wear configuration with the fastening system not fastened.
Figure 4:
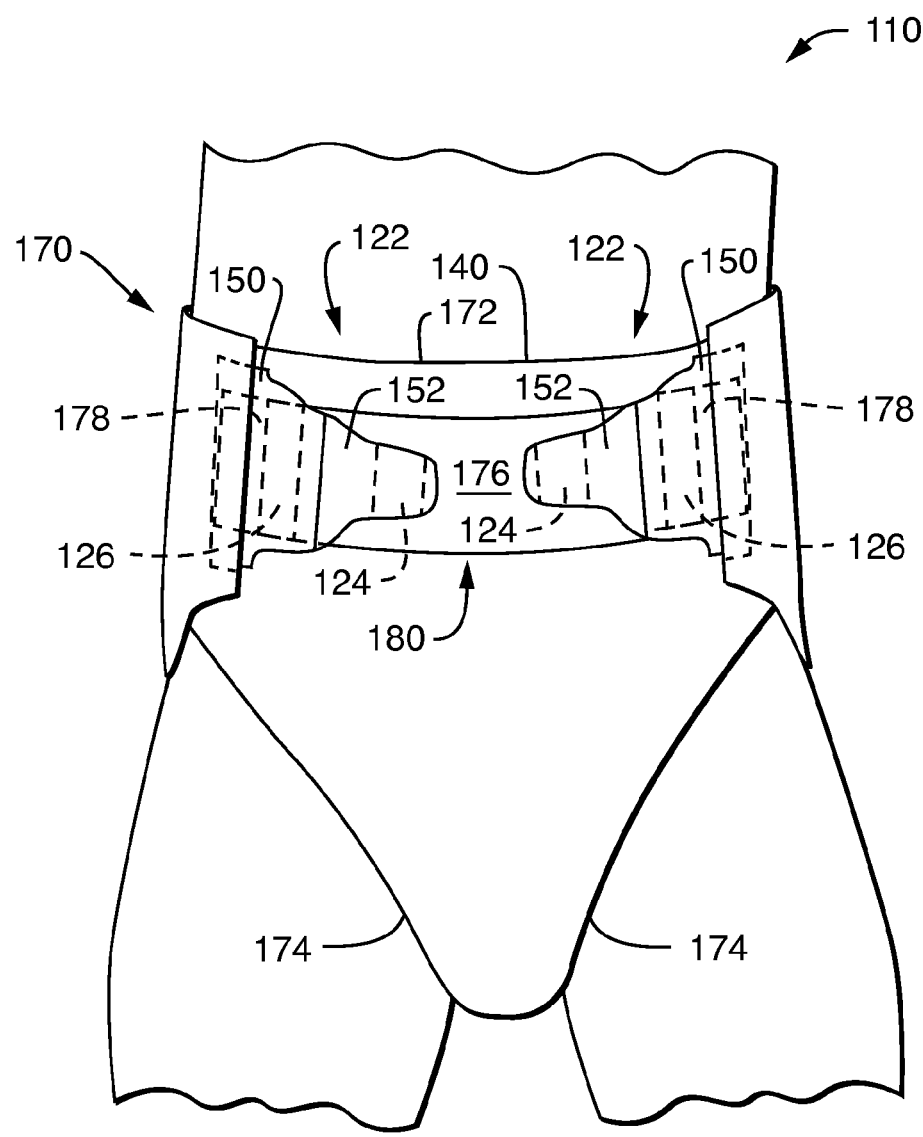
FIG. 4 is a front view of the diaper of FIG. 1 in a wear configuration with the fastening system fastened.

The diaper 110 can be selectively moved from the unfastened configuration, as illustrated in FIGS. 1 and 2, to a fastened or wear configuration as illustrated in FIGS. 3 and 4, by attaching the back waist region 118 (and more specifically the back ears 122) to the front waist region 116 using an article fastening system 170 to define a three-dimensional wear configuration of the diaper having a waist opening 172 and a pair of leg openings 174. Although the diaper 110 illustrated in FIGS. 3 and 4 shows the back waist region 118 (and more specifically the back ears 122) overlapping the front waist region 116 upon connection thereto, which is convenient, the diaper can also be configured so that the front waist region overlaps the back waist region when connected.

According to some aspects, the article fastening system 170 includes a primary fastening system and a secondary fastening system. The primary fastening system includes the primary first fastening components 124 disposed on the non-elastomeric portions 152 of the back ears 122 and at least one corresponding primary second fastening component 176 that is adapted for refastenable engagement to the primary first fastening components. In one suitable aspect, an outer surface of each of the primary fastening components 124, 176 includes a plurality of engaging elements. More specifically, the engaging elements of the primary first fastening components 124 are adapted to repeatedly engage and disengage corresponding engaging elements of the primary second fastening components 176 to releasably secure the diaper 110 in its wear configuration.

The primary fastening components 124, 176 can include any refastenable fasteners suitable for absorbent articles, such as adhesive fasteners, cohesive fasteners, mechanical fasteners, or the like. In one suitable aspect, the primary fastening components 124, 176 include mechanical fastening components, such as hook and loop fasteners. For example, suitable hook and loop components can be provided by interlocking geometric shaped materials. As used herein, "hook" broadly refers to any suitable mechanical fastener adapted to engage loop components including, e.g., hooks, bulbs, mushrooms, arrowheads, balls on stems, stems, structures having stems that engage foam such as open cell foam or the like, etc. Other suitable mechanical fastening components include male and/or female mating components, buckles, snaps, or the like. In the illustrated aspect, the primary first fastening components 124 include hook fasteners and the primary second fastening components 176 include a complementary loop fastener disposed on the outer surface of the outer cover 132. Alternatively, the primary first fastening components 124 can include loop fasteners and the primary second fastening components 176 can include complementary hook fasteners.

The shape, density, and polymer composition of the hooks and loops can be selected to obtain the desired level of engagement between the primary fastening components 124, 176. A more aggressive hook material can include a material with a greater average hook height and/or a greater percentage of directionally-aligned hooks.

In some aspects, the outer facing surface of the outer cover 132 of the diaper 110 is suitably constructed to define the primary second fastening component 176, which is a loop fastener. That is, the outer cover 132 itself can be formed of a material that defines the primary second fastening component 176 (e.g., vertical filament laminate (VFL) or other suitable material).

In another suitable aspect, and as illustrated in FIG. 3, the primary second fastening component 176 can be formed as a separate component and attached to the outer surface of the diaper's outer cover 132. More specifically, a strip, indicated generally at 180, including loop fastening material is attached to the front waist region 116 of the diaper. The strip 180 includes an upper edge 182, a lower edge 184, and a pair of side edges 186 connecting the upper and lower edges 182, 184. The upper edge 182 is spaced from the front waist edge 140 and the side edges 186 are spaced from the respective side edges 128 of the diaper 110.

The secondary fastening system of the article fastening system 170 includes secondary first fastening components 126 and secondary second fastening components 178. The secondary first fastening components 126 are disposed on the front portion 116 of the diaper 110 and are adapted for refastenable engagement to at least one corresponding secondary second fastening component 178 (e.g., the elastomeric portion 150 of the back ears 122). As best seen FIG. 3, in some aspects, the strip 180 can include the pair of spaced-apart secondary first fastening components 126.

In the illustrated aspect, the secondary first fastening components 126 include hook fasteners and are configured to engage the secondary second fastening components 178 in the wear configuration of the diaper 110. Again, as used herein "hook" fasteners refers broadly to any suitable mechanical fastener adapted to engage loop components including, e.g., hooks, bulbs, mushrooms, arrowheads, balls on stems, stems, structures having stems that engage foam such as open cell foam or the like, etc. In one aspect, the secondary first fastening components 126 can be constructed of polyethylene or other suitable polymer blends. In one suitable aspect, the elastomeric portions 150 of the back ears 122 are constructed so at least the inner surfaces of the elastomeric portions define the secondary second fastening components 178 in the form of loop fastening components (i.e., the elastomeric portions and the respective secondary second fastening components are formed integrally). The elastomeric portions 150 in one suitable aspect can be constructed of NBL material so that the elastomeric portions define a loop fastening component. In another suitable aspect, the elastomeric portions 150 can be constructed of VFL material so that the elastomeric portions define a loop fastening component. It is understood, however, that the secondary second fastening components 178 can be formed separately from the elastomeric portions 150 and attached thereto, such as by adhesive, thermal bonds, ultrasonic bonds, pressure bonds, or other suitable techniques without departing from the scope of this disclosure.

In other suitable aspects, the secondary first fastening components 126 can include loop fasteners and the secondary second fastening components 178 can include loop fasteners. Further, in some aspects the secondary first fastening components 126 can be a single, integral fastener. For example, in one suitable aspect the secondary first fastening components 126 can be a single, loop fastener, and the secondary second fastening components 178 can be loop fasteners.

In one suitable aspect, the strip 180 includes both the secondary first fastening components 126 and the primary second fastening component 176. In one such aspect where the primary second fastening component 176 includes a loop material and the secondary first fastening component 126 includes a hook material, the strip 180 can be a suitable loop material (forming the primary second fastening component), and then the hook material can be extruded onto the loop material at two or more locations forming the secondary first fastening components.

In another suitable aspect, the secondary first fastening components 126 can be formed separate from the primary second fastening component 176. In such an aspect, the primary second fastening component 176 can be formed to define the strip 180 and the secondary first fastening components 126 can be attached in overlaying relationship with portions of the primary second fastening component. In such aspects, the secondary first fastening components 126 can be attached to the strip 180 and/or the primary second fastening component 176 using any suitable means known to those skilled in the art, including, e.g., adhesive bonds, ultrasonic bonds, thermal bonds, pressure bonds, and the like, and combinations thereof.

In some aspects, the secondary first fastening components 126 can be attached to the diaper 110 and/or the strip 180 after the strip has been attached to the diaper 110. For example, in one suitable aspect the strip 180 can be first bonded to the diaper 110 using any suitable means as discussed, and then the secondary first fastening components 126 can be bonded to or extruded on the strip. In other aspects, the strip 180 including both the secondary first fastening components 126 and primary second fastening components 176 can be attached to the diaper 110 as one single unit.

According to some aspects, the secondary first fastening components 126 and/or the strip 180 can be sufficiently bonded to the diaper 110 such that a shear force exerted on the secondary first fastening components and/or the strip during use of the diaper does not cause the secondary first fastening components and/or the strip to loosen or completely disengage from the diaper. For example, in some aspects an improved adhesive or the like can be used such that the secondary first fastening components 126 and/or the strip 180 remain securely fastened to, e.g., the outer cover 132 despite the forces exerted on the fastening system 170 during use. In such aspects, the diaper 110 can be less prone to pop-opens and the edges of the secondary first fastening components 126 and/or the strip 180 can remain flush with the outer cover 132 thus reducing irritation during wear that can otherwise be caused by a loose secondary first fastener and/or a loose strip.

When the diaper 110 is moved to the wear configuration (illustrated in FIG. 4) with the primary fastening components 124, 176 engaging one another, the secondary fastening components 126, 178 can also engage one another in order to provide increased stability and leakage protection. For example, because the article fastening system 170 includes four engagement points, the diaper 110 will be less prone to pop-opens when worn. Further, because the secondary fastening components 126, 178 engage each other closer to a side of a wearer than an engagement point of the primary fastening components 124, 176, the secondary fastening system secures the diaper 110 nearer the wearer's sides and legs thus reducing leakage near the leg openings 174 of the diaper. Still further, and again because the secondary fastening components 126, 178 engage each other near a side of the wearer, the secondary fastening system can provide increased stability, thus reducing the occurrence of, e.g., sagging of the diaper due to movement of the wearer.

In some aspects, an appearance of the secondary first fastening component 126, the secondary second fastening component 178, and/or the back ears can be configured to provide suitable visual cues to a user for attaching the diaper 110 to a wearer. For example, in some aspects, a coloring of the secondary first fastening components 126 can be such so as to, e.g., increase the noticeability of the secondary first fastening components on the front portion 116 of the diaper 110. For example, each of the secondary first fastening components 126 can be configured as a different color than its immediate surroundings such that it stands out from its immediate surroundings.

Similarly, a graphic, background pattern, etc., can be removed from the area surrounding the secondary first fastening components 126 to increase the noticeability of each component. Still further, an area on the front portion 116 of the diaper 110 where a corresponding secondary first fastening component 126 attaches can be provided with a different graphic or coloring, etc., than its surrounding, and the secondary first fastening components can correspondingly be constructed of a transparent or semi-transparent material such that, when the secondary first fastening component is provided on the front portion by any suitable means discussed herein, the different coloring, graphical properties, etc., are visible through the secondary first fastening component thus increasing the noticeability of the secondary first fastening components on the front portion.

In still further aspects, the opacity of the pair of back ears 122 and/or the secondary second fastening component 178 can be configured such that each secondary first fastening component 126 is visible through a respective one of the ears 122 when the diaper 110 is in the wear configuration. For example, in some aspects the back ears 122 and/or the secondary second fastening components 178 can be transparent or semi-transparent. In such aspects, the secondary first fastening components 126 can be visible through the back ears 122 when the diaper is in the wear configuration so that a user can be provided with a visual indication of the engagement of each secondary first fastening component with the respective secondary second fastening component 178.

In some aspects, these visual cues (i.e., the coloring or graphical properties of the secondary first fastening component 126 and/or the opacity of the secondary second fastening component 178) can assist a user engaging the secondary fastening system and/or in ensuring the secondary fastening system is properly engaged in the wear configuration.

In other aspects of the present disclosure, the secondary fastening system can have any suitable arrangement. For example, the pair of secondary first fastening components 126 can be disposed directly on the outer cover 132. In another example, each of the secondary first fastening components 126 are provided on a corresponding carrier that is then attached to or otherwise provided on the outer cover 132. In still another example, each of the secondary first fastening components 126 are provided on a corresponding carrier that is then attached to or otherwise provided on the outer cover 132.

In one suitable aspect, the secondary fastening system (and in particular, the secondary first fastening components 126), the back ears 122 (and more particularly, the secondary second fastening component 178), and/or the outer cover 132 of the diaper 110 can be configured such that a peel force (i.e., a force applied by a user or the like of the diaper) needed to disengage the secondary first fastening components from the secondary second fastening components when the diaper is in the wear configuration is much higher than the peel force needed to disengage the secondary first fastening components from the outer cover 132 when the diaper is in the folded configuration. As discussed, when the diaper 110 is provided in the folded configuration, the secondary first fastening components 126 engage the outer cover 132 such that the secondary first fastening components are not exposed to an outside of the diaper and such that the engagement of the secondary first fastening components with the outer cover 132 helps keep the diaper in the folded configuration. However, if the bond between the secondary first fastening components 126 and the outer cover 132 is too great, when the diaper 110 is unfolded for use, the outer cover 132 can tear, delaminate, etc. This can lead to residual pieces of the outer cover 132 remaining on the secondary first fastening components 126 (thus decreasing the effectiveness of the secondary first fastening components) as well as a torn diaper 110 that can leak, provide discomfort to a wearer, and/or that can be aesthetically unappealing to a user.

Accordingly, in some aspects the components of the diaper 110 are configured such that less peel force is needed to disengage the secondary first fastening components 126 from the outer cover 132 to unfold the diaper than is needed to disengage the secondary first fastening components from the back ears 122 (and more particularly from the secondary second fastening components 178). Thus, during use of the diaper 110, less peel force is required to unfold the diaper for use than is needed to remove the diaper from the wear configuration. The lower peel force needed to unfold the diaper 110 makes the diaper easy to open for use without damaging the diaper while the higher peel force needed to remove the diaper from a wearer ensures the diaper remains securely fastened to the wearer over time notwithstanding the wearer crawling, walking, running, bending, etc.

In some aspects, this can be accomplished by configuring the secondary first fastening components 126, the secondary second fastening components 178, and/or the outer cover 132 of the diaper 110 to achieve the desired engagement properties. For example, in aspects where the secondary fastening system is a hook and loop fastening system (i.e., aspects where the secondary first fastening components 126 include hook fasteners and the secondary second fastening components 178 include loop fasteners), the loop properties of the outer cover 132 can be reduced such that the bond between the hooks of the secondary first fastening components and the outer cover 132 is less than the bond between the hooks of the secondary first fastening components and the loops of the secondary second fastening components. Further, in aspects where the secondary fastening system is an adhesive system, the outer cover 132 can be modified to reduce its attachment properties in an area that engages the secondary first fastening components 126 when in the folded state. For example, in some aspects a release coating can be applied to the outer cover 132 in the area that engages the secondary first fastening components 126 when in the folded state. In other aspects, a polymer can be selected for the outer cover 132 that includes the desired attachment properties, and/or one or more polymer additives (such as, e.g., euricimide) can be added to the outer cover 132. Still further, in aspects where the secondary fastening system is a cohesive system, the outer cover 132 can be coated sparingly (or in some aspects not at all) with a cohesive in order to lower the engagement between the secondary first fastening components 126 and the outer cover 132 when in the folded configuration.

This can be more readily understood with reference to a particular example. In some aspects, the secondary first fastening components 126 can be configured such that it is a Velcro-brand or similar polyethylene hook, the secondary second fastening components 178 can be configured such that they are made of NBL, and the outer cover 132 can be constructed such that it is an online laminated outer cover 132 with diamond on diamond bonded spunbond facing. In such aspects, less peel force is needed to disengage the secondary first fastening components 126 from the outer cover 132 of the diaper 110 when in the folded configuration than is needed to disengage the secondary first fastening components from the secondary second fastening components 178 when in the wear configuration. Further, in some aspects less peel force is needed to disengage the secondary first fastening components 126 from the outer cover 132 than fastening components engage the outer cover 132 of known diapers when in the folded configured.

To address the potential for irritation inherent in typical secondary fastener system arrangements, the present disclosure describes a system for shielding the edges of the hook material from contact with the skin of the wearer. The shielding system 200 illustrated in FIGS. 5-7 employs a nonwoven shield 205 coupled to the garment-facing surface of the outer cover 132. Each hook fastening component includes a hook material patch 210 that is disposed between the outer cover 132 and the shield 205. Any suitable additional layers can also be disposed with or near the outer cover 132, shield 205, or hook material patch 210 as needed.

Because the shield 205 could otherwise entirely cover the hook material patch 210, the shield 205 is configured with an aperture 220 therethrough to allow access to the hook material patch 210 resident behind the shield 205. The aperture 220 can be of any curvilinear, rectilinear, or other suitable shape including ovals, circles, squares, and rectangles. The apertures 220 can be formed by die cutting or any other suitable method.

The hook material patch 210 includes a base layer 212 having a hook surface 214 and a non-hook surface 216 opposite the hook surface 214. The hook and non-hook surfaces 214, 216 meet at base layer edges 218. The hook material patch 210 also includes a plurality of hooks 215 affixed to the hook surface 214. The hooks 215 can be uniformly distributed on the hook surface 214, or the hooks 215 can vary in density on the hook surface 214. In one example, the hook surface 214 can include portions having hooks 215, and portions bereft of hooks 215. When placed on the absorbent article 110, some or all of the hooks 215 are accessible from the exterior of the absorbent article 110 via the aperture 220 in the shield 205, while some or all of the base layer edges 218 remain behind the shield 205. Because the base layer edges 218 remain covered by the shield 205, the base layer edges 218 are not exposed to redness-inducing skin contact.

In various aspects, the shield 205 can be bonded to the outer cover 132 or to an interim layer between the shield 205 and the outer cover 132. In addition, the hook material patch 210 can be bonded to the outer cover 132, to the shield 205, or to an interim layer between the hook material patch 210 and the shield 205 or the outer cover 132.

The shield 205 can be formed from the same material as the outer cover 132 as described above, or from any other suitable material. Softness, resistance to tearing, and bulkiness are considerations in selecting a suitable material. In a particular aspect, the shield 205 can be a loop fastener 176 of the type already being employed on the absorbent article 110, and can in fact be a loop fastener that is configured to interact with the primary first fastening component 124. In these aspects, the loop fastener still includes one or more apertures 220 to accommodate the hook material patches 210. In various aspects, the shield or shields 205, loop fasteners, apertures 220, and fasteners associated with the back ears 122 can be arranged in any suitable manner provided the respective components align as described herein.

Figure 5:
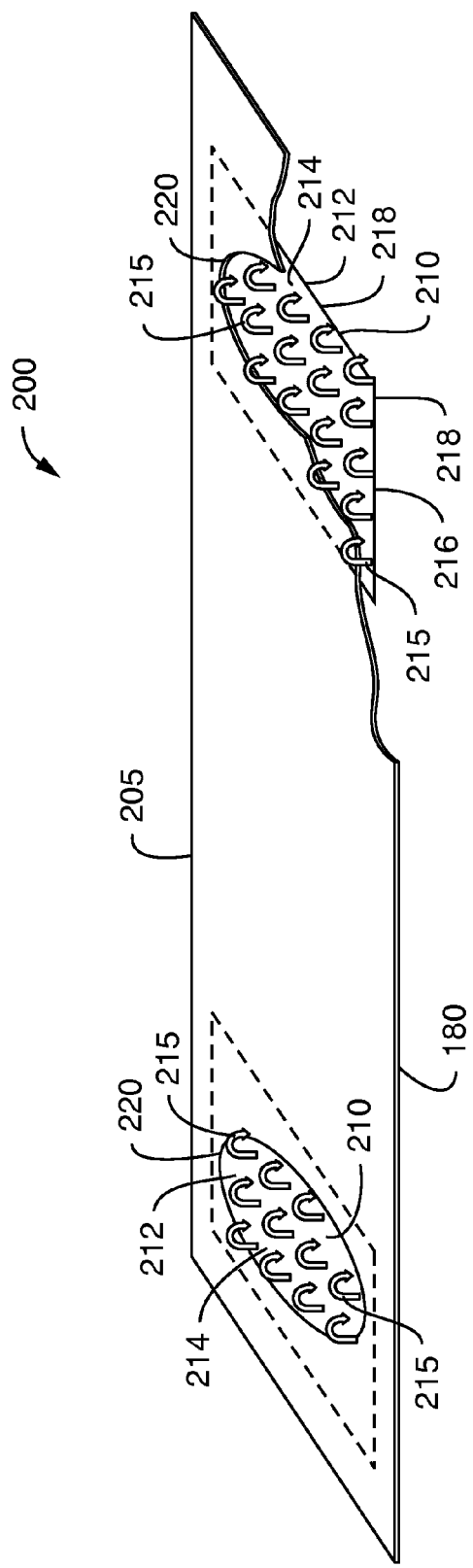
FIG. 5 is a partially cutaway perspective schematic view of a strip to be used in conjunction with the front waist region of the diaper of FIG. 1, illustrating one aspect of a shielding system of the present disclosure.

In one aspect, a single shield 205 can be employed to cover both hook material patches 210, as illustrated in FIG. 5. The single shield 205 will have an aperture 220 for each hook material patch 210. The hook material patch 210 and the shield 205 can be applied in one step to the outer cover 132 of the diaper or by any other suitable means.

Figure 6:
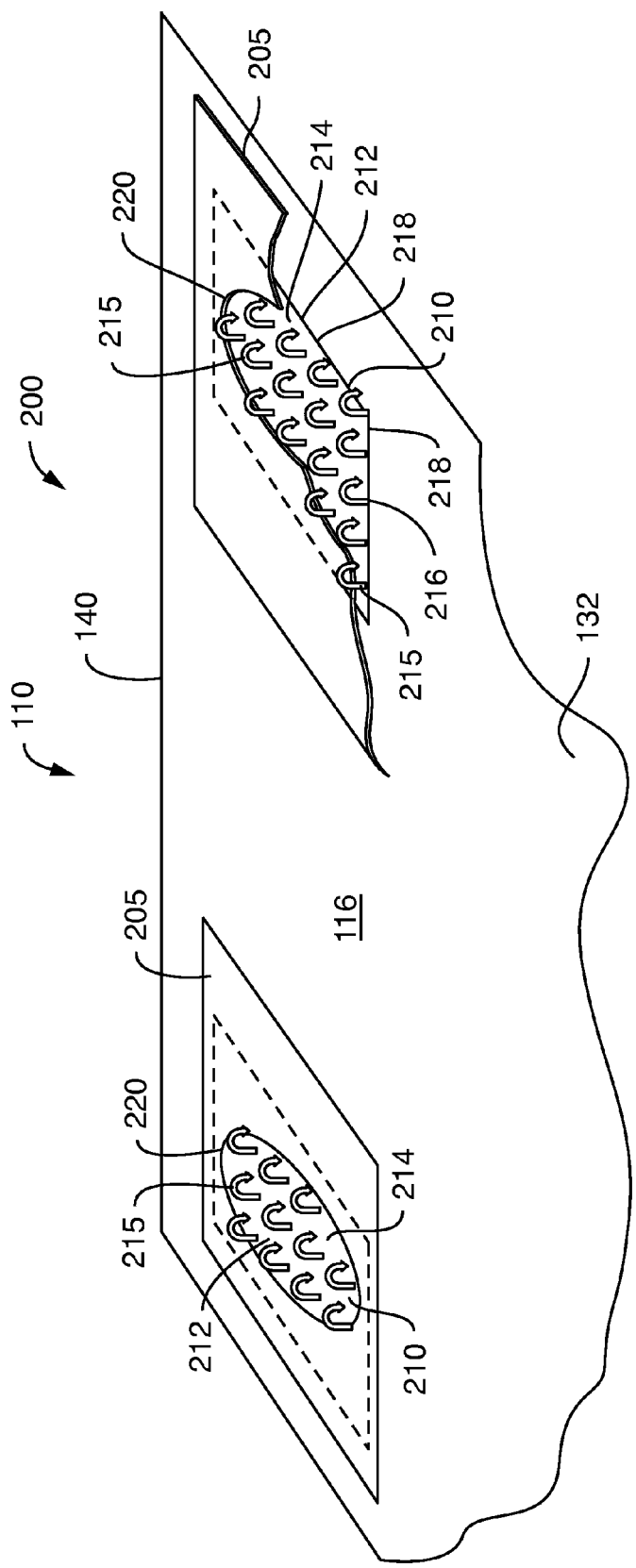
FIG. 6 is a partially cutaway perspective schematic view of a portion of the front waist region of the diaper of FIG. 1, illustrating an alternative aspect of a shielding system of the present disclosure.

In another aspect, two shields 205 can be employed, each covering one of the hook material patches 210, as illustrated in FIG. 6. In this aspect, each shield 205 will have an aperture 220. In each case, the hook material patch 210 and the shield 205 are combined and applied to the absorbent article 110 with a cut and place module, with the hook material patch 210 nested underneath the shield 205.

Figure 7:
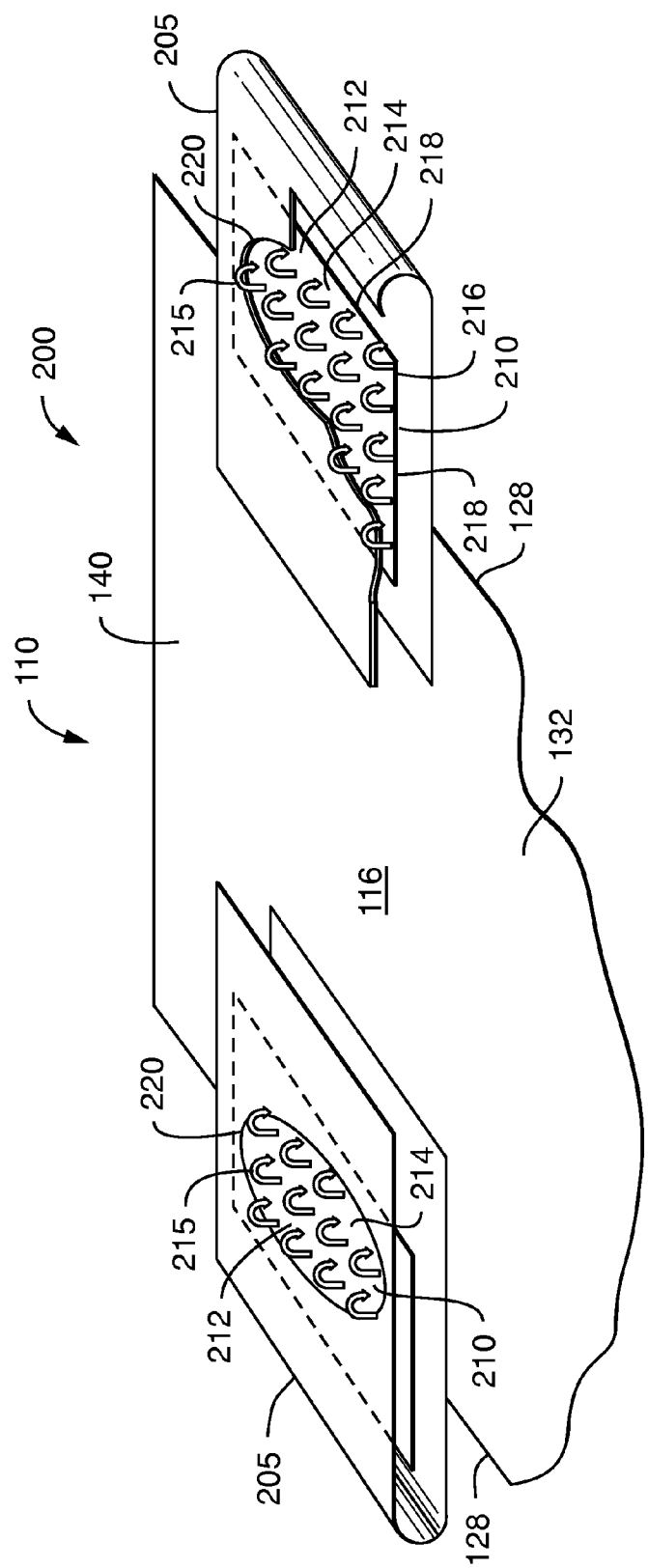
FIG. 7 is a partially cutaway exploded perspective schematic view of a portion of the front waist region of the diaper of FIG. 1, illustrating an alternative aspect of a shielding system of the present disclosure.

In still another aspect illustrated in FIG. 7, a shield 205 can wrap around a hook material patch 210 to cover some or all of the non-hook surface 216 of the hook material patch 210 in addition to some of the hook surface 214 of the hook material patch 210. In this aspect, the shield 205 will still include an aperture 220 to provide access to the hooks 215 on the hook material patch 210. Also in this aspect, the hook material patch 210 can be bonded directly to the shield 205 or to an interim layer between the hook material patch 210 and the shield 205. This aspect also allows the hook material patch/shield combination to be placed such that is extends beyond the side edge 128 of the absorbent article 110, as illustrated in FIG. 7.

The shielding system 200 described herein mitigates the risk for red marking due to hook material coming in contact with a wearer's skin. The apertured shield 205 covers the edges 218 of the hook material with a nonwoven. Each aspect described herein shares the benefit of covering the hook edges 218 to minimize red marking in that all edges and corners of the hook material are covered by soft material.

Prior art absorbent articles have a nonwoven in a first plane (typically the outer cover 132) and hook material in a second plane above (outwardly of) and parallel to the first plane. The aspects described herein have hook material in the first plane and a nonwoven material in a second plane above (outwardly of) and parallel to the first plane to enable the nonwoven material to cover the edges and corners of the hook material.

When introducing elements of the present disclosure or the preferred aspect(s) thereof, the articles "a", "an", "the", and "said" are intended to mean that there are one or more of the elements. The terms "comprising," "including", and "having" are intended to be inclusive and mean that there can be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed:

1. An absorbent article comprising:
   an absorbent assembly including longitudinally opposite ends, transversely opposite sides, a front waist region, a back waist region, and a crotch region extending longitudinally between and interconnecting the front and back waist regions, a liquid permeable bodyside liner for facing a wearer, an outer cover with a garment-facing surface facing away from the wearer, an absorbent body disposed between the bodyside liner and outer cover, at least one of the bodyside liner and outer cover defining the longitudinally opposite ends and transversely opposite sides of the absorbent assembly, the absorbent body having a pair of longitudinally extending sides and a pair of transversely extending ends, each of the longitudinally extending sides of the absorbent body being spaced inward from a respective one of the transversely opposite sides of the absorbent assembly;
   a pair of ears extending transversely outward from the opposite sides of the absorbent assembly in the back waist region, each of the ears comprising a loop fastening component;
   a pair of spaced-apart hook fastening components disposed on the outer cover in the front waist region of the absorbent assembly, each of the hook fastening components being selectively engageable with a respective one of the loop fastening components in a wear configuration of the article; and
   a nonwoven shield coupled to the garment-facing surface of the outer cover, wherein the shield has an aperture therethrough,
   wherein each hook fastening component includes a hook material patch comprising
       a base layer having a hook surface, a non-hook surface opposite the hook surface, and base layer edges therebetween, and
       a plurality of hooks affixed to the hook surface, wherein the hook material patch is disposed between the outer cover and the shield such that at least a portion of the plurality of hooks is accessible through the aperture, and such that at least a portion of the base layer edges is covered by the shield.

2. The article of claim 1, wherein the shield is bonded to the outer cover.

3. The article of claim 1, wherein each hook material patch is bonded to the outer cover.

4. The article of claim 1, wherein the shield includes a loop fastener.

5. The article of claim 1, wherein the shield covers both hook material patches.

6. The article of claim 1, further comprising a second shield, wherein each shield covers one hook material patch.

7. The article of claim 1, wherein the shield wraps around a hook material patch to at least partially cover both the portion of the base layer edges and at least a portion of the non-hook surface.

8. The article of claim 7, wherein the hook material patch is bonded to the shield.

9. The article of claim 1, further comprising a fastening system configured to attach the back waist region to the front waist region to define the wear configuration of the absorbent article, the fastening system comprising a primary fastening system and a secondary fastening system separate from the primary fastening system.

10. The article of claim 9, wherein the secondary fastening system includes the hook fastening components.

11. The article of claim 1, wherein the hook surface of the hook material patch includes areas with hooks affixed and areas without hooks affixed.

12. An absorbent article comprising:
   an absorbent assembly including a front waist region, a back waist region, and a crotch region extending longitudinally between and interconnecting the front and back waist regions, a liquid permeable bodyside liner for facing a wearer, an outer cover with a garment-facing surface facing away from the wearer, and an absorbent body disposed between the bodyside liner and outer cover;
   a pair of ears extending transversely outward from the opposite sides of the absorbent assembly in the back waist region, each of the ears comprising a loop fastening component;
   a pair of spaced-apart hook fastening components disposed on the outer cover in the front waist region of the absorbent assembly, each of the hook fastening components being selectively engageable with a respective one of the loop fastening components in a wear configuration of the article; and a nonwoven shield coupled to the garment-facing surface of the outer cover, wherein the shield has an aperture therethrough, wherein each hook fastening component includes a hook material patch comprising a plurality of hooks and a hook material edge, wherein the hook material patch is disposed between the outer cover and the shield such that at least a portion of the plurality of hooks is accessible through the aperture, and such that a portion of the shield adjacent the aperture covers the hook material edge.

13. The article of claim 12, wherein the shield covers both hook material patches.

14. The article of claim 12, further comprising a second shield, wherein each shield covers one hook material patch.

15. The article of claim 12, wherein the shield wraps around a hook material patch to at least partially enclose the hook material edge.

16. An absorbent article comprising:
 an absorbent assembly including a front waist region, a back waist region, and a crotch region extending longitudinally between and interconnecting the front and back waist regions, a liquid permeable bodyside liner for facing a wearer, an outer cover with a garment-facing surface facing away from the wearer, and an absorbent body disposed between the bodyside liner and outer cover;
 a pair of ears extending transversely outward from the opposite sides of the absorbent assembly in the back waist region, each of the ears comprising a loop fastening component;
 a pair of spaced-apart hook fastening components disposed on the outer cover in the front waist region of the absorbent assembly, each of the hook fastening components being selectively engageable with a respective one of the loop fastening components in a wear configuration of the article; and
 a nonwoven shield coupled to the garment-facing surface of the outer cover, wherein the shield has two curvilinear apertures therethrough,
 wherein each hook fastening component includes a hook material patch comprising
  a base layer having a hook surface, a non-hook surface opposite the hook surface, and base layer edges therebetween, and
  a plurality of hooks affixed to the hook surface, wherein the hook material patch is disposed between the outer cover and the shield such that at least a portion of the plurality of hooks is accessible through an aperture, and such that at least a portion of the base layer edges is covered by the shield.

17. The article of claim 16, wherein the shield wraps around a hook material patch to at least partially enclose the hook material edge.

\* \* \* \* \*